(12) United States Patent
O'Lenick, Jr. et al.

(10) Patent No.: US 6,372,934 B1
(45) Date of Patent: Apr. 16, 2002

(54) WATER SOLUBLE COMPLEXES

(75) Inventors: Anthony J. O'Lenick, Jr., Dacula, GA (US); Charles W. Buffa, Paterson, NJ (US)

(73) Assignee: BioSil Research Institute, Paterson, NJ (US)

( * ) Notice: Subject to any disclaimer, the term of this patent is extended or adjusted under 35 U.S.C. 154(b) by 0 days.

(21) Appl. No.: 09/483,899

(22) Filed: Jan. 18, 2000

(51) Int. Cl.[7] ......................... C07C 69/76; C07C 69/34
(52) U.S. Cl. ......................... 560/89; 560/198
(58) Field of Search ..................... 560/89, 198

(56) References Cited

U.S. PATENT DOCUMENTS 5,300,287 A * 4/1994 Park

FOREIGN PATENT DOCUMENTS

| EP | 580435 | * | 1/1994 |
| JP | 130509 | * | 10/1979 |
| WO | 9636871 | * | 11/1996 |

OTHER PUBLICATIONS

Evstratova, N.G. et al. Bioorg. Khim (1979) 5(8) 1140–1145.*

* cited by examiner

Primary Examiner—Paul J. Killos

(57) ABSTRACT

The invention relates to a series of novel salt complexes that are made by neutralizing a fatty ammonium compound which is cationic with an anionic compound, producing a salt complex. The compounds of the present invention are water soluble, non-irritating to the eye and skin and are well suited to personal care applications.

20 Claims, No Drawings

WATER SOLUBLE COMPLEXES

BACKGROUND OF THE INVENTION

1. Field of the Invention

The invention relates to a series of novel salt complexes that are made by neutralizing a fatty ammonium compound which is cationic with an anionic compound, producing a salt complex, and an inorganic salt. The compounds of the invention are water soluble, non-irritating to the eye and skin and are well suited to personal care applications.

2. Arts and Practices

Fatty quaternary compounds commonly called quats, are tetra-substituted ammonium compounds where each of the four groups on nitrogen are a group other than hydrogen. If any hydrogen groups are present, the compounds are not quaternary amines, but rather are primary or secondary amines.

The most commonly encountered substituents are alkyl and alkyl amido groups. There are several classes of quats. The most important are (a) alkyl tri methyl quats for example cetyltrimonium chloride, (b) alkylamidopropyl dimethyl quats like stearylamidalkonium chloride and (c) di alkyl, di methyl quats for example dicetyldimonium chloride and (d) alkyl, benzyl, Di methyl quats like stearalkonium chloride.

There are several undesirable attributes of fatty cationic products.

1. Fatty Quaternary compounds are incompatible with anionic surfactants since an insoluble complex frequently is formed when the two types of materials are combined.

2. Many fatty Quaternary Compounds are eye irritants. The material is minimally irritating to the eyes at concentrations of 2.5%, which limits the concentration which is useful if low irritation is a requirement.

3. Fatty quats are generally hydrophobic and when applied to substrate can cause a loss of absorbance of the substrate. It is not an uncommon situation for a traveler to a hotel to encounter a very soft towel that totally fails to absorb water. This is because the fatty quaternary gives softness but being hydrophobic also prevents re-wet. This situation also can be observed on hair, the conditioner becomes gunky on the hair and has a tendency to build up.

We have learned that many of these negative attributes can be unexpectantly mitigated by making fatty complexes with carboxy fatty alcohol alkoxylates. The preferred complex has to have a molecular weight of over 1000 molecular weight units to obtain the most effective irritation mitigation. The mitigation of irritation, the improved water solubility and the skin feel make the compounds of the present invention highly desirable in personal care applications.

THE INVENTION

OBJECT OF THE INVENTION

It is the object of the present invention to provide a series of novel salt complexes that are made by neutralizing a fatty ammonium compound which is cationic with an anionic compound, producing a salt complex having a molecular weight above 1000 molecular weight units. The compounds of the invention are water soluble, non-irritating to the eye and skin and are well suited to personal care applications.

SUMMARY OF THE INVENTION

The invention relates to a series of novel salt complexes that are made by neutralizing a fatty ammonium compound which is cationic with an anionic compound, producing a salt complex having a molecular weight above 1000 molecular weight units. The compounds of the invention are water soluble, non-irritating to the eye and skin and are well suited to personal care applications.

DETAILED DESCRIPTION OF THE INVENTION

The compounds of the present invention conform to the following structure:

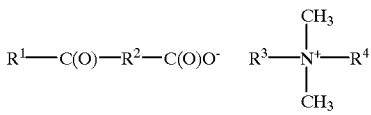

wherein;

$R^1$ is $CH_3-(CH_2)_n-O-(CH_2CH_2O)_a-(CH_2CH(CH_3)O)_b-(CH_2CH_2O)_c-$;

n is an integers ranging from 7 to 21;

a and c are integers independently ranging from 0 to 20, with the proviso that a+b be greater than 5;

b is an integer ranging from 0 to 20;

$R^2$ is selected from the group consisting of $-CH_2-CH_2-$, $-CH=CH-$, and

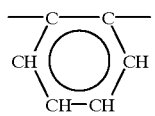

$R^3$ is selected from the group consisting of

and

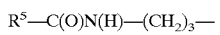

$R^5$ is $CH_3(CH_2)_f-$ e is an integer from 5 to 21;

f is an integer from 5 to 21;

$R^4$ is selected from the group consisting of

g is an integer ranging from 0 to 21 and

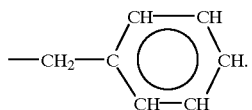

PREFERRED EMBODIMENTS

In a preferred embodiment $R^1$ is;
$CH_3-(CH_2)_n-O-(CH_2CH_2O)_a-(CH_2CH(CH_3)O)_b-(CH_2CH_2O)_c-$.

In a preferred embodiment $R^2$ is $-CH_2-CH_2-$.

In a preferred embodiment $R^2$ is $-CH=CH-$.

In a preferred embodiment $R^2$ is

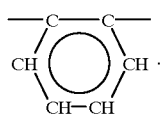

In a preferred embodiment e is an integer ranging from 7 to 21.
In a preferred embodiment $R^3$ is;
  $R^5C(O)N(H)$—$(CH_2)_3$—
    f is an integer ranging from 5 to 21.
In a preferred embodiment $R^4$ is methyl.
In a preferred embodiment $R^4$ is

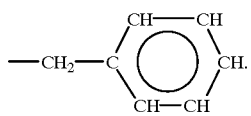

In a preferred embodiment the molecular weight of the complex is greater than 1000.
In another preferred embodiment, the complex is blended with dimethicone copolyol to improve the skin feel.

EXAMPLES OF REACTANTS

ANHYDRIDES

The various anhydrides listed are all items of commerce and are prepared by methods known to those skilled in the art.

Reactant Example I (Succinic Anhydride)

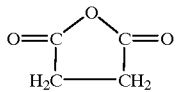

Reactant Example II (Maleic Anhydride)

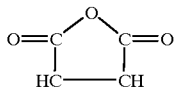

Reactant Example III (Phthalic Anhydride)

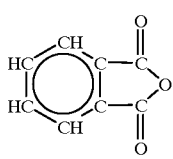

The reaction sequence is illustrated by the reaction with succinic anhydride:

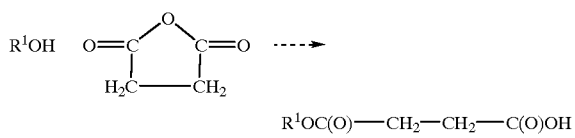

Raw Materials

Alkoxylated alcohols suitable for the preparation of the compounds of the present invention are commercially available from Siltech Corporation in Toronto Ontario Canada.

$R^1$—C(O)—$R^2$—C(O)OH

| Example | n | a | b | c |
|---|---|---|---|---|
| 1 | 8 | 0 | 0 | 5 |
| 2 | 10 | 0 | 1 | 12 |
| 3 | 12 | 20 | 10 | 20 |
| 4 | 14 | 3 | 1 | 3 |
| 5 | 16 | 20 | 20 | 20 |
| 6 | 18 | 12 | 0 | 0 |
| 7 | 20 | 12 | 1 | 1 |
| 8 | 22 | 5 | 0 | 5 |

General Reaction Conditions

Into a suitable round bottom, three neck flask equipped with a thermometer and a nitrogen sparge is added the specified number of grams of the specified alcohol alkoxylate compound and the specified number of grams of the specified anhydride. The reaction mass is blanketed with nitrogen, and heated to 80 and 110° C. under the inert nitrogen blanket. Within four to five hours the theoretical acid value is obtained. The product is a clear liquid and is used without additional purification.

EXAMPLES 9–14

Succinic Derivatives

Into a suitable round bottom, three neck flask equipped with a thermometer and a nitrogen sparge is added the specified number of grams of the specified alcohol alkoxylate (examples 1–8) compound and the 100.0 grams of succinic anhydride. The reaction mass is blanketed with nitrogen, and heated to 80° and 110° C. under the inert nitrogen blanket. Within four to five hours the theoretical acid value is obtained. The product is a clear liquid and is used without additional purification.

| Example | Alcohol Example | Alkoxylate Grams |
|---|---|---|
| 9 | 1 | 391.0 |
| 10 | 2 | 742.0 |
| 11 | 3 | 2533.0 |
| 12 | 4 | 447.0 |
| 13 | 5 | 3179.0 |
| 14 | 6 | 795.0 |
| 15 | 7 | 926.0 |
| 16 | 8 | 763.0 |

EXAMPLES 17–24

Maleic Derivatives

Into a suitable round bottom, three neck flask equipped with a thermometer and a nitrogen sparge is added the specified number of grams of the specified alcohol alkoxylate (examples 1–8) compound and the 98.0 grams of maleic anhydride. The reaction mass is blanketed with nitrogen, and heated to 80° and 110° C. under the inert nitrogen blanket. Within four to five hours the theoretical acid value is obtained. The product is a clear liquid and is used without additional purification.

| Example | Alcohol Example | Alkoxylate Grams |
|---|---|---|
| 17 | 1 | 391.0 |
| 18 | 2 | 742.0 |
| 19 | 3 | 2533.0 |
| 20 | 4 | 447.0 |
| 21 | 5 | 3179.0 |
| 22 | 6 | 795.0 |
| 23 | 7 | 926.0 |
| 24 | 8 | 763.0 |

EXAMPLES 25–32

Phthalic Derivatives

Into a suitable round bottom, three neck flask equipped with a thermometer and a nitrogen sparge is added the specified number of grams of the specified alcohol alkoxylate (examples 1–8) compound and the 146.0 grams of phthalic anhydride. The reaction mass is blanketed with nitrogen, and heated to 80° and 110° C. under the inert nitrogen blanket. Within four to five hours the theoretical acid value is obtained. The product is a clear liquid and is used without additional purification.

| Example | Alcohol Example | Alkoxylate Grams |
|---|---|---|
| 25 | 1 | 391.0 |
| 26 | 2 | 742.0 |
| 27 | 3 | 2533.0 |
| 28 | 4 | 447.0 |
| 29 | 5 | 3179.0 |
| 30 | 6 | 795.0 |
| 31 | 7 | 926.0 |
| 32 | 8 | 763.0 |

CATIONIC EXAMPLES

The cationic compounds of the present invention are commercially available from a variety of sources including Croda Inc. and Siltech Corporation.

They conform to the following structure:

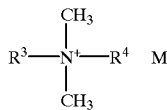

wherein;

$R^3$ is selected from the group consisting of $CH_3(CH_2)_e-$ and $R^5-C(O)N(H)-(CH_2)_3-$ $R^5$ is $CH_3(CH_2)_f-$ e is an integer from 5 to 21;

f is an integer from 5 to 21;

$R^4$ is selected from the group consisting of $CH_3(CH_2)_g$ g is an integer ranging from 0 to 21 and

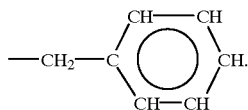

M is selected from the group consisting of $Cl^-$, $Br^-$, and $CH_3SO_4-$.

As used herein

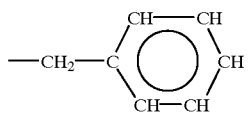

is referred to as benzyl.

| Class 1 Cationic Compounds | | |
|---|---|---|
| | e | g |
| 33 | 7 | 0 |
| 34 | 11 | 0 |
| 35 | 17 | 0 |
| 36 | 17 | 0 |
| 37 | 21 | 0 |
| 38 | 21 | benzyl |

M is $Cl^-$

| Class 2 Cationic Compounds | | |
|---|---|---|
| | e | g |
| 39 | 7 | 7 |
| 40 | 11 | 7 |
| 41 | 15 | 21 |
| 42 | 17 | 3 |
| 43 | 21 | 5 |
| 44 | 17 | benzyl |
| 45 | 21 | benzyl |

M is $Cl^-$

| Class 3 Cationic Compounds $R3$ is $R^5C(O)N(H)-(CH2)3-$ | | |
|---|---|---|
| Example | f | g |
| 46 | 7 | 0 |
| 47 | 9 | 0 |
| 48 | 11 | 0 |
| 59 | 17 | 11 |
| 50 | 21 | 21 |
| 51 | 17 | Benzyl |
| 52 | 5 | 11 |

M is $Cl^-$

Complexation

The carboxy fatty alcohol alkoxylate (examples 9–32) and the cationic compound (examples 33–52) are blended into water to make up a concentration of between 20–70%. The preferred range is 30–50% by weight. The pH of the resulting mixture is then adjusted to between 5 and 9. The lower pH is preferred for skin care products, the higher for hair care products. The complex forms in aqueous solution and the counter ion on the cationic material remains in the solution as inorganic salt.

EXAMPLE 53

To a suitable vessel is added 840.0 grams of water. Next 491.0 grams of anionic compound Example 9 is added under agitation. Next 209.0 grams of cationic compound 33 is added. The pH is adjusted to 7.0 with KOH. The complex is used as prepared.

EXAMPLES 54–76

Example 53 is repeated, only this time the specified amount of water. Next the specified amount of the specified anionic compound is added. Next the specified amount of the specified cationic compound is added. The pH is adjusted to 7.0 with KOH. The complex is used as prepared.

| Example | Anionic Compound Example | Compound Grams | Cationic Compound Example | Compound Grams | Water Grams |
|---|---|---|---|---|---|
| 54 | 10 | 842.0 | 34 | 265.0 | 1328.0 |
| 55 | 11 | 2633.0 | 35 | 349.0 | 3578.0 |
| 56 | 12 | 547.0 | 36 | 373.0 | 1104.0 |
| 57 | 13 | 3279.0 | 37 | 405.0 | 4420.0 |
| 58 | 14 | 895.0 | 38 | 416.0 | 1704.0 |
| 56 | 15 | 1026.0 | 39 | 293.0 | 1582.0 |
| 60 | 16 | 863.0 | 40 | 349.0 | 1515.0 |
| 61 | 17 | 489.0 | 41 | 601.0 | 1635.0 |
| 62 | 18 | 840.0 | 42 | 377.0 | 1292.0 |
| 63 | 19 | 2631.0 | 43 | 416.0 | 3656.0 |
| 64 | 20 | 545.0 | 44 | 389.0 | 1167.0 |
| 65 | 21 | 3277.0 | 45 | 445.0 | 4466.0 |
| 66 | 22 | 893.0 | 46 | 280.0 | 1257.0 |
| 67 | 23 | 1024.0 | 47 | 308.0 | 1600.0 |
| 68 | 24 | 861.0 | 48 | 336.0 | 1436.0 |
| 69 | 25 | 537.0 | 49 | 574.0 | 1333.0 |
| 70 | 26 | 888.0 | 50 | 770.0 | 1812.0 |
| 71 | 27 | 2679.0 | 51 | 511.0 | 3992.0 |
| 72 | 28 | 593.0 | 52 | 406.0 | 1250.0 |
| 73 | 29 | 3325.0 | 51 | 511.0 | 5754.0 |
| 74 | 30 | 941.0 | 50 | 770.0 | 2053.0 |
| 75 | 31 | 1072.0 | 49 | 574.0 | 1646.0 |
| 76 | 32 | 909.0 | 45 | 445.0 | 1760.0 |

Applications Evaluation

Control Compounds

Stearalkonium Chloride is an excellent conditioning agent, having outstanding substantivity to hair. It has detangling properties, improves wet comb when applied after shampooing. The FDA formulation data for 1976 reports the use of this material in 78 hair conditioners, eight at less than 0.1%, eighteen at between 0.1 and 1.0% and 52 at between 1 and 5%.

Cetyltrimonium Chloride, or CTAC, is a very substantive conditioner which in addition having a non-greasy feel, improves wet comb and also provides a gloss to the hair. It is classified as a severe primary eye irritant.[18] Therefore its use concentration is generally at or below 1%.

Eye Irritation

Eye irritation is a major concern in the formulation of personal care products, particularly when working with quats. Primary eye irritation was tested using the protocol outlined in FHSLA 16 CFR 1500.42. The products were tested at 25% actives. The results were as follows:

| Cationic Compounds (Not of the Present Invention) | | |
|---|---|---|
| Stearalkonium Chloride | 116.5 | Severely Irritating |
| Cetyltrimethyl ammonium Chloride | 106.0 | Severely Irritating |
| Cetyltriethyl ammonium Chloride | 115.0 | Severely irritating |
| Complexes of the Present Invention | | |
| Example 56 | 8.1 | Minimally Irritating |
| Example 61 | 11.3 | Minimally Irritating |
| Example 62 | 10.2 | Minimally Irritating |
| Example 70 | 4.9 | Minimally Irritating |
| Example 76 | 7.8 | Minimally Irritating |

As the data clearly shows, the irritation potential of the complex is dramatically reduced, when compared to the starting quat.

What is claimed is:

1. A complex conforming to the following structure:

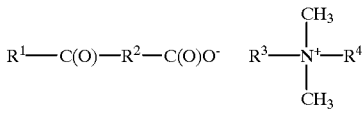

wherein;

$R^1$ is $CH_3—(CH_2)_n—O—(CH_2CH_2O)_a—(CH_2CH(CH_3)O)_b—(CH_2CH_2O)_c—$;

n is an integer ranging from 7 to 21;

a and c are integers independently ranging from 0 to 20, with the proviso that a+b be greater than 5;

b is an integer ranging from 0 to 20;

$R^2$ is selected from the group consisting of $—CH_2—CH_2—$, $—CH=CH—$, and

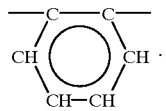

$R^3$ is selected from the group consisting of

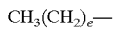

and

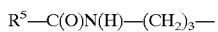

$R^5$ is $CH_3(CH_2)_f—$ e is an integer from 5 to 21;

f is an integer from 5 to 21;

$R^4$ is selected from the group consisting of

g is an integer ranging from 0 to 21 and

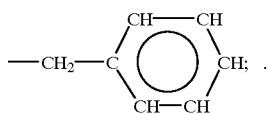

2. A complex of claim 1 wherein
R$^1$ is

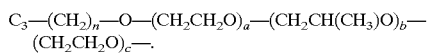

3. A complex of claim 2 wherein
R$^2$ is

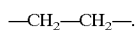

4. A complex of claim 2 wherein
R$^2$ is

—CH=CH—.

5. A complex of claim 2 wherein
R$^2$ is

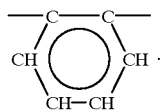

6. A complex of claim 3 wherein R$^3$ is alkyl having 8 to 22 carbon atoms.
7. A complex of claim 4 wherein
e is an integer ranging from 7 to 21.
8. A complex of claim 5 wherein
e is an integer ranging from 7 to 21.
9. A complex of claim 3 wherein
R$^3$ is;

R$^5$C(O)N(H)—(CH2)3—

R$^5$ is alkyl having 5 to 21 carbon atoms.
10. A complex of claim 4 wherein
R$^3$ is;

R$^5$C(O)N(H)—(CH$_2$)$_3$—

R$^5$ is alkyl having 5 to 21 carbon atoms.
11. A complex of claim 5 wherein
R$^3$ is;

R$^5$C(O)N(H)—(CH$_2$)$_3$—

R$^5$ is alkyl having 5 to 21 carbon atoms.
12. A complex of claim 6 wherein R$^4$ is methyl.
13. A complex of claim 7 wherein R$^4$ is methyl.
14. A complex of claim 8 wherein R$^4$ is methyl.
15. A complex of claim 9 wherein R$^4$ is methyl.
16. A complex of claim 10 wherein R$^4$ is methyl.
17. A complex of claim 11 wherein R$^4$ is methyl.
18. A complex of claim 6 wherein R$^4$ is

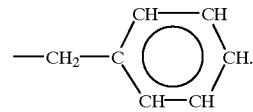

19. A complex of claim 7 wherein R$^4$ is

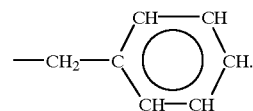

20. An carboxy compound conforming to the following structure:

R$^1$—C(O)—R$^2$—C(O)OH wherein;
R$^2$ is selected from the group consisting of —CH$_2$—CH$_2$—, —CH=CH—, and

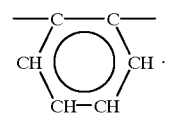

* * * * *